United States Patent [19]

Foricher et al.

[11] Patent Number: 5,302,738
[45] Date of Patent: Apr. 12, 1994

[54] CHIRAL PHOSPHINES

[75] Inventors: Joseph Foricher, Mulhouse, France; Bernd Heiser, Inzlingen, Fed. Rep. of Germany; Rudolf Schmid, Arlesheim, Switzerland

[73] Assignee: Hoffmann-La Roche Inc., Nutley, N.J.

[21] Appl. No.: 949,878

[22] PCT Filed: Mar. 12, 1992

[86] PCT No.: PCT/CH92/00050

§ 371 Date: Nov. 13, 1992

§ 102(e) Date: Nov. 13, 1992

[87] PCT Pub. No.: WO92/16535

PCT Pub. Date: Oct. 1, 1992

[30] Foreign Application Priority Data

Mar. 15, 1991 [CH] Switzerland .................. 794/91

[51] Int. Cl.$^5$ .................. C07F 9/40; C07F 9/52
[52] U.S. Cl. .................. 558/162; 568/13
[58] Field of Search .................. 558/162, 147; 568/13

[56] References Cited

U.S. PATENT DOCUMENTS

| | | | |
|---|---|---|---|
| 3,897,491 | 7/1975 | Toy et al. | 562/811 |
| 4,495,111 | 1/1985 | Guerin et al. | 558/162 |
| 4,556,740 | 12/1985 | Hansen et al. | 568/13 |
| 4,876,269 | 10/1989 | Pennev et al. | 514/429 |
| 4,952,598 | 8/1990 | Lerch et al. | 514/414 |
| 5,223,632 | 6/1993 | Ishizaki et al. | 556/21 |

FOREIGN PATENT DOCUMENTS 0398132 5/1990 Fed. Rep. of Germany .

2140659 6/1972 France .

OTHER PUBLICATIONS

Greene, T. W. *Protective Groups in Organic Synthesis*; John Wiley and Sons: New York, 1981, pp. 10, 14–16.

*Primary Examiner*—Mary C. Lee
*Assistant Examiner*—Michael G. Ambrose
*Attorney, Agent, or Firm*—George M. Gould; William H. Epstein

[57] ABSTRACT

Novel, racemic and optically active phosphorus compounds of the formula

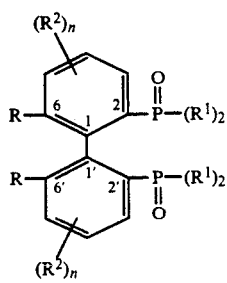

I wherein R signifies lower alkyl, lower alkoxy or protected hydroxy, $R^1$ signifies lower alkoxy, phenoxy, benzyloxy, chlorine or bromine, $R^2$ stands for lower alkyl or lower alkoxy and n represents the number 0, 1 or 2, are described. These compounds are valuable intermediates in the manufacture of not only known, but also novel diphosphine ligands.

10 Claims, No Drawings

CHIRAL PHOSPHINES

The present invention is concerned with novel, racemic and optically active phosphorus compounds of the general formula

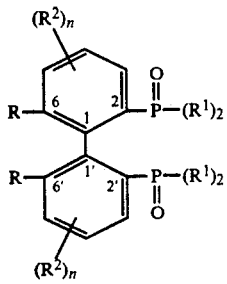

wherein R signifies lower alkyl, lower alkoxy or protected hydroxy, $R^1$ signifies lower alkoxy, phenoxy, benzyloxy, chlorine or bromine, $R^2$ stands for lower alkyl or lower alkoxy and n represents the number 0, 1 or 2.

The invention is also concerned with the manufacture of the phosphorus compounds of formula I.

The term "lower alkyl" signifies in the scope of the present invention straight-chain or branched alkyl groups with 1 to 4 carbon atoms such as methyl, ethyl, propyl, isopropyl, n-butyl, isobutyl and tert.butyl. The term "lower alkoxy" signifies groups in which the alkyl residue has the foregoing significance. The terms "phenoxy" and "benzyloxy" signify in the scope of the present invention substituents in which the phenyl residue can be not only unsubstituted, but also substituted in the meta- or para-position or also poly-substituted. Lower alkyl groups, preferably methyl groups, especially come into consideration here as substituents. As protecting groups for the hydroxy group there come into consideration in the scope of the present invention especially the usual ether-forming groups such as e.g. benzyl, allyl, benzyloxymethyl, lower alkoxymethyl, 2-methoxyethoxymethyl and the like.

The phosphorus compounds of formula I can be present not only in racemic form, but also in optically active form. Of those compounds of formula I in which R represents lower alkyl the optically active compounds are preferred.

Preferred compounds of formula I are, moreover, those in which n stands for the number 0, $R^1$ signifies phenoxy, ethoxy or chlorine and R represents methoxy, methoxymethyl or methyl, especially methoxy.

Especially preferred compounds of formula I are:
(RS)-(6,6'-Dimethoxybiphenyl-2,2'-diyl)bis(phosphonic acid diphenyl ester),
(R)- or (S)-(6,6'-dimethoxybiphenyl-2,2'-diyl)bis(phosphonic acid diphenyl ester),
(RS)-(6,6'-dimethoxybiphenyl-2,2'-diyl)bis(phosphonic acid diethyl ester),
(R)- or (S)-(6,6'-dimethoxybiphenyl-2,2'-diyl)bis(phosphonic acid diethyl ester),
(RS)-[6,6'-bis(methoxymethoxy)biphenyl-2,2'-diyl]bis(phosphonic acid diphenyl ester),
(R)- or (S)-[6,6'-bis(methoxymethoxy)biphenyl-2,2'-diyl]bis(phosphonic acid diphenyl ester),
(RS)-(6,6'-dimethylbiphenyl-2,2'-diyl)bis(phosphonic acid diphenyl ester),
(R)- or (S)-(6,6'-dimethylbiphenyl-2,2'-diyl)bis(phosphonic acid diphenyl ester),
(RS)-(6,6'-dimethylbiphenyl-2,2'-diyl)bis(phosphonic acid diethyl ester),
(R)- or (S)-(6,6'-dimethylbiphenyl-2,2'-diyl)bis(phosphonic acid diethyl ester),
(RS)-(6,6'-dimethoxybiphenyl-2,2'-diyl)bis(phosphonic acid dichloride),
(R)- or (S)-(6,6'-imethoxybiphenyl-2,2'-diyl)bis(phosphonic acid dichloride).

The compounds of formula I in accordance with the invention can be manufactured, for example, by subjecting a compound of the formula

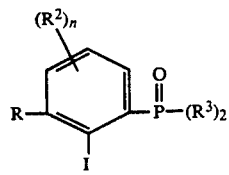

wherein R, $R^2$ and n have the above significance and $R^3$ signifies lower alkoxy, phenoxy or benzyloxy, to an Ullmann coupling, if desired resolving a thus-obtained compound of the formula

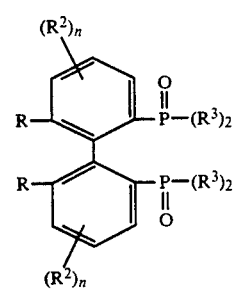

wherein R, $R^2$, $R^3$ and n have the above significance, which is present in the (RS) form into the (R) form and (S) form using dibenzoyltartaric acid or di-p-toluyltartaric acid and, if desired, replacing a lower alkoxy group denoted by $R^3$ in a racemic or optically active compound of formula III by chlorine or bromine.

The conversion of a compound of formula II into a compound of formula III which is present in the (RS) form is effected in accordance with the invention by means of an Ullmann coupling. This is a reaction which is known per se and which can be carried out under the conditions which are usual for this. Thus, this reaction can be carried out, for example, by heating a compound of formula II in an inert organic solvent such as e.g. N,N-dimethylformamide with e.g. copper powder activated with iodine to a temperature of about 110° C. to about 200° C. If desired, the reaction can also be carried out in the absence of a solvent, i.e. in the melt.

The compounds of general formula II which are used as starting materials are novel and are also an object of the present invention. When R is different from lower alkyl, they can be prepared, for example, by subjecting a compound of the general formula

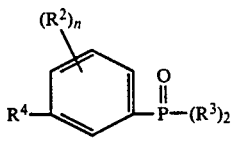

IV wherein $R^2$, $R^3$ and n have the above significance and $R^4$ signifies lower alkoxy or protected hydroxy, to an otho-lithiation/iodination reaction.

The ortho-lithiation of a compound of formula IV can be effected in a manner known per se. For example, this reaction can be effected by reacting a compound of formula IV with a lithium amide, e.g. lithium diisopropylamide or lithium 2,2,6,6-tetramethylpiperidine, in tetrahydrofuran at a temperature below 0° C., preferably at about −50° C. to about −78° C. The subsequent iodination can be effected conveniently with molecular iodine, with ICl or IBr, likewise in tetrahydrofuran and likewise at a temperature below −50° C.

Those starting materials of formula II in which R signifies lower alkyl can be prepared, for example, starting from a compound of the formula

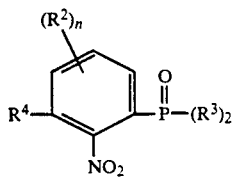

V wherein $R^2$, $R^3$ and n have the above significance and $R^4$ represents lower alkyl.

This is conveniently effected by the generally known reduction of the nitro group to the amino group, e.g. by means of hydrogen in the presence of a catalyst such as, for example, Pd/C, and subsequent diazotization/iodination in a manner known per se.

The compounds of formulae IV and V which are also used as starting materials are known compounds or analogues of known compounds which can be prepared readily in a manner known per se; compounds IV e.g. in accordance with J. J. Monagle et al., J. Org. Chem. 32, 2477 (1967) and compounds V e.g. in accordance with K. S. Petrakis et al., J. Am. Chem. Soc. 1987, 109, 2831.

The racemate resolution of a compound of III which is present in the (RS) form by means of (−)- or (+)-O,O'-dibenzoyltartaric acid (DBT) or (−)- or (+)-O,O'-di-p-toluyltartaric acid (DTT) can be carried out in an analogous manner to the racemate resolution of phosphine oxides, although this actually was unexpected having regard to the state of the art. This is conveniently effected in an inert organic solvent and at a temperature of about 0° C. to about 60° C. As solvents there can be mentioned here especially chloroform, methylene chloride, ethyl acetate, isopropyl acetate, acetone, alcohols such as methanol or ethanol and the like, as well as mixtures thereof.

The thus-obtained adducts of the compounds of formula III with (−)- or (+)-DBT or DTT can subsequently be treated with an inorganic base in an analogous manner to phosphine oxide adducts, whereby the respective (R) or (S) form of the compounds of formula III is liberated.

When $R^3$ signifies lower alkoxy in a racemic or optically active compound of formula III, this can be replaced by chlorine or bromine. This substitution can be effected in a manner known per se, for example by reaction with thionyl chloride, thionyl bromide or phosphorus pentachloride in an inert organic solvent.

Alternatively, those compounds of formula III in which R represents lower alkyl can be obtained starting from compounds of the formula

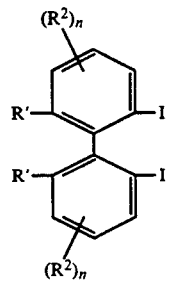

VI wherein $R^2$ and n have the above significance and R' represent lower alkyl.

This can be effected in a manner which is simple and known per se, e.g. by reacting a compound of formula VI with a compound of the formula

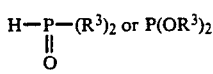

wherein $R^3$ has the above significance, in the presence of a tert. amine such as, for example, triethylamine and a catalyst such as e.g. $Pd(P\text{-}(phenyl)_3)_4$ or in the presence of a catalyst such as e.g. $PdCl_2$ or $NiCl_2$.

Compounds of formula I, especially the optically active forms, are valuable intermediates in the manufacture of not only known, but also novel diphosphine ligands. Furthermore, these are valuable building bricks of complexes with transition metals, especially with metals of Group VIII such as, for example, ruthenium, rhodium or iridium, which serve as catalysts in, inter alia, asymmetric hydrogenations.

The compounds of formula I can be converted readily into the mentioned diphosphine ligands. In this case it must only be taken into consideration that, when compounds of formula I in which $R^1$ signifies lower alkoxy are used, the lower alkoxy group is preferably firstly replaced by chlorine or bromine.

The conversion is conveniently effected by reaction with an aryl- or heteroaryl-Grignard or lithium compound of the formula

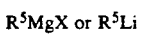

wherein X represent chlorine, bromine or iodine, whereby there is obtained a compound of the formula

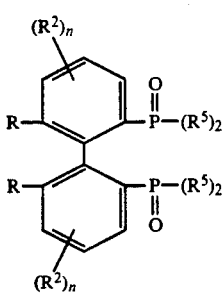

VII wherein R, R² and n have the foregoing significance and R⁵ signifies, for example, phenyl, substituted phenyl or α-furyl, which is subsequently reduced to a diphosphine ligand of the formula

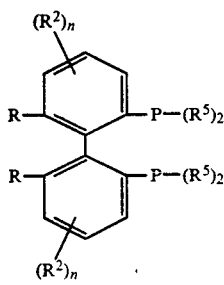

VIII wherein R, R², n and R⁵ have the foregoing significance.

Depending on the significance especially of the substituents R⁵ the compounds of formula VIII are known or novel diphosphine ligands.

The reaction of a compound of formula I with R⁵MgX or R⁵Li can be effected in a manner known per se. Preferably, this is effected e.g. under the usual conditions of a Grignard reaction. Preferably, compounds of formula I in which R¹ represents phenoxy are reacted with a compound of the formula R⁵MgX and those in which R¹ represents chlorine or bromine are reacted with a compound of the formula R⁵-Li or R⁵MgX.

The reduction of a racemic compound of formula VII or of a compound of formula VII which is present in (R) or (S) form can be carried out in a manner known per se. This can be effected, for example, with silanes such as e.g. trichlorosilane in an aromatic hydrocarbon such as, for example, in boiling xylene or in acetonitrile etc., conveniently in the presence of an auxiliary base such as, for example, triethylamine or preferably tributylamine. If desired, this reduction can also be carried out in an autoclave under pressure.

With respect to the compounds of formula III in which R represents lower alkyl, it is generally preferred to carry out the racemate resolution only at the stage of the subsequent compounds of formula VII or VIII. However, also in this case, the racemate resolution can be carried out in manner known per se, e.g. in accordance with the method described by S. Otsuka et al., in J. Am. Chem. Soc. 1971, 93, 4301.

All previously mentioned reactions—with the exception of the racemate resolution—are conveniently carried out under an inert gas such as e.g. argon or nitrogen.

In analogy to the manufacture and use of the compounds of formula I, compounds of the binaphthyl type of the following formula

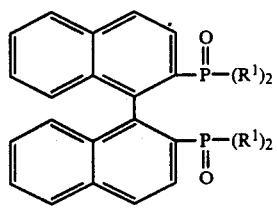

IX wherein R¹ has the above significance, can likewise be manufactured and used. The binaphthyl rings can be substituted in the usual manner.

The following Examples serve to illustrate the invention and in no manner represent any limitation. In these Examples the selected abbreviations have the following significance:

| TLC: | thin layer chromatography |
|---|---|
| DBT: | O,O'-Dibenzoyltartaric acid |

All temperatures are given in °Celsius.

EXAMPLE 1 a) 76.5 g (0.122 mol) of (2-iodo-3-methoxyphenyl)-phosphonic acid diphenyl ester (75% pure) and 25.0 g (0.393 mol) of activated copper powder were placed under argon in a 1 l four-necked sulphonation flask provided with a condenser, thermometer, stirrer and headpiece for inert gas treatment and 200 ml of N,N-dimethylformamide were allowed to flow in. The dark brown suspension was heated at 140° (oil bath temperature) for 1 hour, after which time complete conversion had taken place according to TLC analysis. The cooled reaction mixture was transferred into a round flask with methylene chloride and evaporated to dryness at 70° on a rotary evaporator. The residue was treated with 200 ml of methylene chloride, the mixture was stirred well and filtered, and the filter residue was washed with 100 ml of methylene chloride. The filtrate was washed three times with 100 ml of sat. NH₄Cl solution, whereby a small amount of solid formed was filtered off in the first wash operation, and subsequently dried over MgSO₄, filtered and concentrated. After drying in a high vacuum (~10 Pa) for 2 hours at 80° there were obtained 59.6 g of crude (RS)-(6,6'-dimethoxybiphenyl-2,2'-diyl)-bis(phosphonic acid diphenyl ester).

ba) A solution of 59.6 g of the crude diphenyl ester obtained in accordance with a) in 50 ml of dichloromethane was placed in a 1 l round flask and treated with a solution of 35.8 g (0.10 mol) of (−)-O,O'-dibenzoyl-L-tartaric acid in 100 ml of ethyl acetate. The solution was then evaporated on a rotary evaporator at 600 mbar, whereby the CH₂Cl₂ distilled off and a white solid separated. This was filtered off under suction, washed three times with 20 ml of ethyl acetate and 20 ml of hexane and dried in a high vacuum (~10 Pa). There were obtained 21.8 g of (R)-diphenyl ester/(−)-DBT adduct as a white powder. [α]$_D^{20}$ = −95.6 (c=1 in ethanol).

The mother liquors and wash solutions were placed on one side in order to obtain the other enantiomer.

bb) The material obtained in accordance with ba) was triturated with 100 ml of dichloromethane, 50 ml of sat.

NaHCO$_3$ solution and 50 ml of deionized water in a 1 l Erlenmeyer flask having a mag-netic stirrer until all of the solid had passed into solution (30 minutes). The phases were separated and the organic phase was washed twice with 100 ml of semi-sat. NaHCO$_3$ solution, 50 ml of deionized water and 50 ml of sat. NaCl solution, dried over MgSO$_4$, filtered and evaporated. The oily residue was treated with 20 ml of tert.-butyl methyl ether, whereby crystallization set in. After evaporation and drying in a high vacuum ($\sim$10 Pa) for 1 hour at 60° there were obtained 13.8 g of (R)-(6,6'-dimethoxybiphenyl-2,2'-diyl)bis(phosphonic acid diphenyl ester) as white crystals. M.p. 125°-125.5°; $[\alpha]_D^{20} = -18.9$ (c=1 in CHCl$_3$).

ca) The mother liquors and wash solutions from ba) were evaporated in a 1 l round flask. The residue was taken up in 100 ml of dichloromethane and the solution was triturated for 30 minutes with 50 ml of sat. NaHCO$_3$ solution and 50 ml of deionized water. The phases were separated and the organic phase was washed with 100 ml of semi-sat. NaHCO$_3$ solution, 50 ml of deionized water and 50 ml of sat. NaCl solution, dried over MgSO$_4$, filtered and concentrated. The brown oil obtained was taken up in 50 ml of dichloromethane and the solution was treated with a solution of 18.0 g (0.050 mol) of (+)-O,O'-dibenzoyl-D-tartaric acid in 100 ml of ethyl acetate. The solution was then concentrated on a rotary evaporator at 600 mbar, whereby the CH$_2$Cl$_2$ distilled off and white solid separated. This was filtered off under suction, washed three times with 20 ml of ethyl acetate and 20 ml of hexane and dried in a high vacuum ($\sim$10 Pa). There were obtained 22 g of (S)-diphenyl ester/(+)-DBT adduct as a light yellowish powder. $[\alpha]_D^{20} = +96$ (c=1 in ethanol).

cb) The material obtained in accordance with ca) was worked-up as described in bb). There were obtained 13.9 g of (S)-(6,6'-dimethoxybiphenyl-2,2'-diyl)bis(phosphonic acid diphenyl ester) as white crystals. M.p. 124°-125°; $[\alpha]_D^{20} = +18.7$ (c=1 in CHCl$_3$).

d) The (2-iodo-3-methoxyphenyl)phosphonic acid diphenyl ester used as the starting material was prepared as follows:

daa) A suspension of 13.0 g (0.535 mol) of magnesium shavings in 50 ml of dry tetrahydrofuran was placed under argon in a 0.5 l four-necked flask provided with a stirrer, condenser, thermo-meter and headpiece for inert gas treatment. Thereto there was added dropwise within 90 minutes a solution of 93.5 g (0.50 mol) of 3-bromoanisole in 200 ml of dry tetrahydrofuran in such a manner that the reaction temperature did not exceed 35°. After the addition the mixture was diluted with an additional 150 ml of dry tetrahydrofuran in order to prevent the precipitation of the Grignard reagent.

dab) 259.8 g (0.967 mol) of diphenyl chlorophosphate and 200 ml of dry tetrahydrofuran were placed in a 1.5 l four-necked flask provided with a stirrer, thermometer, headpiece for inert gas treatment and CO$_2$/acetone cooling bath and the solution was cooled to $-78°$. Thereto there was now added dropwise the solution of the Grignard reagent prepared in accordance with baa) in such a manner that the reaction temperature did not exceed $-70°$. After completion of the addition the mixture was left to warm to room temperature overnight while stirring. The reaction mixture, which contained some fine white precipitate, was poured into a mixture of 2 l of ice-water, 2 l of sat. NaHCO$_3$ solution and 1 l of diethyl ether in a 10 l stirring vessel. After vigourous stirring for 10 minutes the aqueous phase was separated and the organic phase was washed in succession with 1 l of sat. NaHCO$_3$ solution, 200 ml of 25% ammonia, 100 ml of 25% ammonia and three times with 500 ml of sat. NaCl solution. After drying over MgSO$_4$ the solution was evaporated, the residue was taken up in 1 l of diethyl ether and the solution was left to stand at 0° overnight. The white solid (12 g) which thereby separated was removed by filtration and discarded. The filtrate was evaporated, dried in a high vacuum ($\sim$10 Pa), the residue obtained (163 g of yellow oil) was taken up in 300 ml of hexane/toluene 1:1 and the solution was filtered over 500 g of silica gel. By elution firstly with 3 l of hexane and 8 l of hexane/ethyl acetate 9:1 and thereafter with 2 l of hexane/ethyl acetate 4:1 and 2 l of hexane/ethyl acetate 7:3 there were obtained, after drying in a high vacuum ($\sim$10 Pa) for 1 hour at 40°, 118 g of (3-methoxyphenyl)phosphonic acid diphenyl ester as a slightly yellowish oil.

db) 300 ml of dry tetrahydrofuran were placed in a 1.5 l four-necked flask provided with a stirrer, thermometer, headpiece for inert gas treatment, dropping funnel with pressure balance and CO$_2$/acetone cooling bath. 70 ml (0.412 mol) of 2,2,6,6-tetramethylpiperidine were added thereto using a syringe and the solution was cooled to $-78°$. 210 ml (0.336 mol) of 1.6N butyllithium solution in hexane were filled into the dropping funnel via a steel canula. The butyllithium solution was dropped into the reaction vessel within about 10 minutes, whereby the temperature rose to about $-50°$ and a white precipitate formed. The CO$_2$/acetone cooling bath was replaced by an ice/ethanol bath and the reaction mixture was stirred at about $-15°$ for a further 30 minutes, then again cooled to $-78°$.

250 ml of dry tetrahydrofuran and 95.2 g (0.280 mol) of (3-methoxyphenyl)phosphonic acid diphenyl ester (material from dab) were placed under argon in a separate 1 l round flask and the solution was cooled to $-78°$. This solution was now allowed to flow via a steel canula into the above reaction mixture within about 10 minutes, whereby the temperature rose to about $-68°$ and a translucent, caramel-coloured solution resulted. This was stirred at $-78°$ for a further 30 minutes.

A solution of 71.06 g (0.280 mol) of iodine in 150 ml of dry tetrahydrofuran was prepared under argon in a separate 250 ml Schlenk tube and the solution was transferred via a steel canula into the dropping funnel of the reaction apparatus. The reaction mixture was now titrated within 15 minutes by the rapid dropwise addition of the iodine solution, whereby the reaction temperature rose to $-65°$. After the dropwise addition of about 145 ml of the about 170 ml of iodine solution, when a red coloration of the reaction mixture remained, the addition was interrupted and the mixture was left to warm to 0°. Then, the reaction mixture was treated with 150 ml of a solution of 100 g of sodium thiosulphate pentahydrate in 200 ml of deionized water, stirrer vigorously and subsequently treated with 100 ml of sat. NaHCO$_3$ solution. The two-phase system was filtered in order to remove the precipitate formed and the phases were separated. The aqueous phase was re-extracted once with 250 ml of ethyl acetate and the combined organic phases were washed with 250 ml of sat. NaCl solution, dried over MgSO$_4$ and evaporated. The residue was taken up in 500 ml of ethyl acetate and the solution was washed three times with 250 ml of deionized water and with 250 ml of sat. NaCl solution, dried over MgSO$_4$, filtered and concentrated. The residue (118 g of yellow oil) was taken up in 170 ml of toluene and the solution was treated with 115 ml of hexane, whereby a white precipitate separated. This was removed by filtration and the filtrate was applied to a column of 450 g of silica gel. Byproducts were firstly eluted with 2 l of hexane/ethyl acetate 9:1 and 3 l of hexane/ethyl acetate 8:2. Subsequently, fractions containing the end product were eluted with 2 l of hexane/ethyl acetate 7:3. After evaporation and drying in a high vacuum (~10 Pa) for 1 hour at 60° there were obtained 76.5 g of an orange oil. This consisted in accordance with $^1$H-NMR analysis of 75 mol % of (2-iodo-3-methoxyphenyl)phosphonic acid diphenyl ester.

EXAMPLE 2

The following compounds were manufacture in an analogous manner to Example 1:

(RS)-(6,6'-Dimethoxybiphenyl-2,2'-diyl)bis(phosphonic acid diethyl ester). M.p. 145°–146°.

(S)-(6,6'-Dimethoxybiphenyl-2,2'-diyl)bis(phosphonic acid diethyl ester). M.p. 125°–126°; $[\alpha]_D{}^{20} = -33.3$ (c=1 in CHCl$_3$).

(R)-(6,6'-Dimethoxybiphenyl-2,2'-diyl)bis(phosphonic acid diethyl ester). M.p. 125°–126°; $[\alpha]_D{}^{20} = +32.7$ (c=1 in CHCl$_3$).

(2-Iodo-3-methoxyphenyl)phosphonic acid diethyl ester. M.p. 99°–101°.

(RS)-[6,6'-Bis(methoxymethoxy)biphenyl-2,2'-diyl]-bis(phosphonic acid diethyl ester).

(R)-[6,6'-Bis(methoxymethoxy)biphenyl-2,2'-diyl]-bis(phosphonic acid diethyl ester). M.p. 119°–120°; $[\alpha]_D{}^{20} = -22$ (c=1 in CHCl$_3$).

(S)-[6,6'-Bis(methoxymethoxy)biphenyl-2,2'-diyl]-bis(phosphonic acid diethyl ester). M.p. 118°–119°; $[\alpha]_D{}^{20} = +20.6$ (c=1 in CHCl$_3$).

[2-Iodo-3-(methoxymethoxy)phenyl]phosphonic acid diethyl ester.

EXAMPLE 3

A solution of 2.43 g (5.0 mmol) of (RS)-(6,6'-dimethoxyphenyl-2,2'-diyl)bis(phosphonic acid diethyl ester) (prepared in accordance with Example 2), 3.63 ml (5.93 g, 50 mmol) of thionyl chloride and 0.38 ml of dry N,N-dimethylformamide was boiled at reflux under argon for 3 hours. The excess thionyl chloride was subsequently distilled off and the residue was dried in a high vacuum (~10 Pa) at 100° for 1 hour. The viscous oil obtained was taken up in 15 ml of CH$_2$Cl$_2$. After filtering off a small amount of insoluble material, the filtrate was treated with 20 ml of ether, whereby a white powder separated. Filtration, washing with ether and drying in a high vacuum (~10 Pa) yielded 1.60 g of (RS)-(6,6'-dimethoxybiphenyl-2,2'-diyl)bis(phosphonic acid dichloride) of m.p. 195°–198°.

The following compounds were manufactured in an analogous manner to the foregoing:

(R)-(6,6'-Dimethoxybiphenyl-2,2'-diyl)bis(phosphonic acid dichloride). M.p. 172°–178°; $[\alpha]_D{}^{20} = +51.3$ (c=1 in CHCl$_3$).

(S)-(6,6'-Dimethoxybiphenyl-2,2'-diyl)bis(phosphonic acid dichloride). M.p. 172°–178°; $[\alpha]_D{}^{20} = -50.2$ (c=1 in CHCl$_3$).

EXAMPLE 4

The following compound was manufactured in an analogous manner to Example 1a):

(RS)-(6,6'-Dimethylbiphenyl-2,2'-diyl)bis(phosphonic acid diethyl ester) as a yellowish oil.

$^1$H-NMR; 250 MHz/CDCl$_3$): 7.83 (dd,J=7.5, 14.5, 2 arom. H); 7.45–7.30 (m, 4 arom. H); 4.0–3.6 (m, 2 P(OCH$_2$CH$_3$)$_2$); 1.99 (s, 2 CH$_3$); 1.14 (t, J=7, 2 P(OCH$_2$CH$_3$)$_2$).

MS (198,037): 454 (71, M+), 317 (100, M+-P(O)(OEt)$_2$).

The (2-iodo-3-methylphenyl)phosphonic acid diethyl ester used as the starting material was prepared as follows:

a) 15.52 g (55 mmol) of trifluoromethanesulphonic anhydride were added dropwise within 30 minutes at −5° to a solution of 7.66 g (50 mmol) of 3-methyl-2-nitrophenol in 50 ml of pyridine. The reaction mixture was stirred at −5° to room temperature overnight, diluted with ether and poured into ice-water. The organic phase was separated, washed with 1N HCl, sat. NaHCO$_3$ solution and sat. NaCl solution, dried over Na$_2$SO$_4$, filtered and evaporated. The residue was filtered with hexane/ether 1:1, whereafter there were obtained 12 g of trifluoromethanesulphonic acid (2-nitro-3-methylphenyl ester) as colourless crystals of m.p. 24°–26°.

b) A mixture of 1.43 g (5.0 mmol) of trifluoromethanesulphonic acid (2-nitro-3-methylphenyl ester), 0.76 g (5.5 mmol) of diethyl phosphite, 0.76 g (7.5 mmol) of triethylamine, 0.20 g (0.173 mmol) of tetrakis(triphenyl-phosphine)palladium and 5 ml of toluene was heated at 90° for 40 hours. The dark yellow solution was treated with ether and H$_2$O, the phases were separated and the organic phase was washed with H$_2$O, 2N HCl, sat. NaHCO$_3$ solution and sat. NaCl solution, dried over Na$_2$SO$_4$, filtered and evaporated. Chromatography on silica gel (hexane/ethyl acetate 25–40%) yielded 0.906 g of 2-nitro-3-methylphenylphosphonic acid diethyl ester as a yellow liquid.

c) A solution of 3.62 g (13.25 mmol) of 2-nitro-3-methylphenylphosphonic acid diethyl ester in 50 ml of ethanol was hydrogenated in the presence of 200 mg of 5% Pd/C under 1 atm. of H$_2$. After 6 hours the mixture was diluted with ethyl acetate, filtered over a small amount of SiO$_2$ and evaporated, whereafter 3.31 g of (2-amino-3-methylphenyl)phosphonic acid diethyl ether were obtained as a reddish oil.

d) A solution of 914 mg (13.25 mmol) of NaNO$_2$ in 5 ml of H$_2$O was added dropwise within 20 minutes at 0° to a solution of 3.31 g (13.25 mmol) of (2-amino-3-methylphenyl)phosphonic acid diethyl ester in 12 ml of 50% H$_2$SO$_4$. After an additional stirring period of 10 minutes the reaction mixture was covered with 10 ml of ether and a solution of 3.30 g (19.88 mmol) of KI in 12.5 ml of H$_2$O was added dropwise at 0°–5°. After completion of the addition the mixture was treated with 10 ml of ether and the two-phase system was stirred at 0° to room temperature for a further 2 hours. For the working-up, the mixture was treated with a small amount of Na$_2$S$_2$O$_3$ and with ether and H$_2$O, the phases were separated and the organic phase was washed with 2N HCl, H$_2$O, sat. NaHCO$_3$ solution and sat. NaCl solution, dried over Na$_2$SO$_4$, filtered and evaporated. Chromatography on silica gel (hexane/ethyl acetate 1:1) followed by crystallization from 20 ml of hexane/2 ml of ether at −15° yielded 3.47 g of (2-iodo-3-methylphenyl)phosphonic acid diethyl ester as white crystals of m.p. 56°–58°.

EXAMPLE 5

A mixture of 4.40 g (10.1 mmol) of (RS)-2,2'-diiodo-6,6'-dimethylbiphenyl, 75 mg (0.42 mmol) of PdCl$_2$ and 4.07 g (24.5 mmol) of triethyl phosphite was heated to 160° (bath temperature) while stirring. The ethyl bromide formed was distilled off over a distillation bridge with the aid of a weak $N_2$ stream. After periods of in each case 1 hour the reaction mixture was treated with a further three portions of 4.07 g (24.5 mmol) of triethyl phosphite each time. After 5 hours the excess triethyl phosphite was distilled off in a high vacuum ($\sim$10 Pa) at 80°–100°. The residual brown oil was chromatographed on silica gel (hexane/ethyl acetate 1:1, then ethyl acetate/EtOH 0%→10%), whereby there were obtained 1.80 g of (RS)-(6,6'-dimethylbiphenyl-2,2'-diyl)-bis(phosphonic acid diethyl ester). The analytical sample was distilled in a bulb tube at about 220° (0.2 mbar).

IR (410 409/120; film): 1245 (P=O); 1056, 1026 (P-O), 784 (1,2,3-trisubst. benzene).

$^1$H-NMR (303 747; 250 MHz/CDCl$_3$): 7.83 (dd, J=7.5, 14.5, 2 arom. H); 7.45–7.30 (m. 4 arom. H); 4.03–3.6 (m, 2 P(OCH$_2$CH$_3$)$_2$); 1.99 (s, 2 CH$_3$); 1.14 (t, J=7, 2 P(OCH$_2$CH$_3$)$_2$).

MS (249 430): 454 (70, M+), 317 (100, M+-[P(O)(O-Et)$_2$]).

EXAMPLE 6

20 g (46.07 mmol) of (RS)-2,2'-diiodo-6,6'-dimethylbiphenyl, 23.72 g (101.3 mmol) of diphenyl phosphite, 12 g (119 mmol) of triethylamine and 2.62 g (2.26 mmol) of Pd(PPh$_3$)$_4$ were heated at 100° for 20 hours in a Schlenk tube while stirring. Thereafter, the reaction mixture was concentrated on a rotary evaporator, the residue was dissolved in CH$_2$Cl$_2$ and treated with NaOH solution. The organic phase was washed with water and dried over Na$_2$SO$_4$. The residue obtained after concentration of the organic phase was recrystallized from methanol. There were obtained 21.1 g of (RS)-(6,6'-dimethylbiphenyl-2,2'-diyl)bis(phosphonic acid diphenyl ester) as a pale beige powder.

IR (KBr): 1592, 1490, 1277, 1214, 1185, 1157, 926, 764, 733, 687.

$^1$H-NMR (250 MHz, CDCl$_3$): 8.12–6.74 (m, 26 aromat. H), 1.98 (s, 2 aromat. CH$_3$).

MS: 646 (0.3, M+); 553 (100, M+—OC$_6$H$_5$); 413 (M+—P(O)(O$_6$H$_5$)$_2$.

EXAMPLE 7 a) 678 mg (10 mmol) of (R)-(6,6'-dimethoxybiphenyl-2,2'-diyl)bis(phosphonic acid diphenyl ester) (prepared in accordance with Example 1) were introduced at room temperature into a phenylmagnesium bromide solution prepared from 1.57 g (10 mmol) of bromobenzene and 243 mg (10 mmol) of magnesium shavings in 10 ml of tetrahydrofuran. The reaction mixture was stirred at room temperature for 30 minutes and subsequently boiled under reflux for 2 hours. For the working-up, the mixture was treated with 50 ml of sat. NH$_4$Cl solution and 50 ml of ethyl acetate, the phases were separated and the organic phase was washed with sat. NaCl solution, dried over MgSO$_4$, filtered and concentrated. The residue was dissolved in a small amount of CH$_2$Cl$_2$ and the solution was applied to a column of 50 g of silica gel. Elution with ethyl acetate and then with tetrahydrofuran yielded a white powder which was recrystallized from CH$_2$Cl$_2$/tert.-butyl methyl ether. There were obtained 510 mg of (R)-(6,6'-dimethoxybiphenyl-2,2'-diyl)bis(diphenylphoshine oxide). M.p. 337° (thermoanalysis); $[\alpha]_D^{20}=+128.4$ (c=1, CHCl$_3$).

b) A 0.51 four-necked sulphonation flask provided with a condenser, thermometer, dropping funnel and mechanical stirrer was charged under argon with 4.50 g (6.12 mmol) of (R)-(6,6'-dimethoxybiphenyl-2,2'-diyl)-bis(diphenylphosphine oxide), 10 ml (41.9 mmol) of tributylamine, 60 ml of a xylene isomer mixture and 4.0 ml (5.37 g, 39.6 mmol) of trichloroxylene. The milky-white mixture was boiled under reflux for 4 hours, whereby an almost translucent solution resulted. After cooling 100 ml of deoxygenated 30% sodium hydroxide solution were added while stirring while in such a manner that the internal temperature did not exceed 70° and the mixture was stirred at 70° for a further 1 hour. After the addition of H$_2$O and CH$_2$Cl$_2$ the phases were separated and the organic phase was washed with 2×50 ml of 30% sodium hydroxide solution, H$_2$O, sat. NH$_4$Cl solution and NaCl solution, dried over MgSO$_4$, filtered and evaporated. The white powder obtained (4.40 g) was dissolved in CH$_2$Cl$_2$, the solution was treated with ethanol and the CH$_2$Cl$_2$ was evaporated on a rotary evaporator. The precipitated solid was filtered off, washed with ethanol and pentane and dried in a high vacuum ($\sim$10 Pa) for 1 hour at 100°. There were obtained 3.90 g of (R)-(6,6'-dimethoxybiphenyl-2,2'-diyl)-bis(diphenylphosphine) as white crystals; m.p. 214°–215°; $[\alpha]_D^{20}=+42.4$ (c=1, CHCl$_3$).

The following compounds were prepared in an analogous manner:

(S)-(6,6'-Dimethoxybiphenyl-2,2'-diyl)bis(diphenylphosphine oxide). M.p. 336.5° (thermoanalysis); $[\alpha]_D^{20}=-130.4$ (c=1, CHCl$_3$).

(S)-(6,6'-Dimethoxybiphenyl-2,2'-diyl)bis(diphenylphosphine). M.p. 214°–215°; $[\alpha]_D^{20}=-41.7$ (c=1, CHCl$_3$).

(RS)-(6,6'-Dimethoxybiphenyl-2,2'-diyl)bis(di-p-tolylphosphine oxide). M.p. 300° (thermoanalysis).

(RS)-(6,6'-Dimethoxybiphenyl-2,2'-diyl)bis(di-p-tolylphosphine). M.p. 247°–249°.

(R)-(6,6'-Dimethoxybiphenyl-2,2'-diyl)bis(di-p-tolylphosphine oxide). M.p. 318°; $[\alpha]_D^{20}=+103.5$ (c=1, CHCl$_3$).

(S)-(6,6'-Dimethoxybiphenyl-2,2'-diyl)bis(di-p-tolylphosphine oxide). M.p. 321°; $[\alpha]_D^{20}=-105$ (c=1, CHCl$_3$).

(R)-(6,6'-Dimethoxybiphenyl-2,2'-diyl)bis(di-p-tolylphosphine). M.p. 209°–210°; $[\alpha]_D^{20}=+33.2$ (c=1, CHCl$_3$).

(S)-(6,6'-Dimethoxybiphenyl-2,2'-diyl)bis(di-p-tolylphosphine). M.p. 208°–209°; $[\alpha]_D^{20}=-32.5$ (c=1, CHCl$_3$).

(RS)-(6,6'-Dimethoxybiphenyl-2,2'-diyl)bis[bis(p-methoxyphenyl)phosphine oxide]. M.p. 282°–283°.

(RS)-(6,6'-Dimethoxybiphenyl-2,2'-diyl)bis[bis(p-methoxyphenyl)phosphine].

(R)-(6,6'-Dimethoxybiphenyl-2,2'-diyl)bis[bis(p-methoxyphenyl)phosphine oxide]. M.p. 213°–214°; $[\alpha]_D^{20}=+92.5$ (c=1, CHCl$_3$).

(S)-(6,6'-Dimethoxybiphenyl-2,2'-diyl)bis[bis(p-methoxyphenyl)phosphine oxide]. M.p. 207°–208°; $[\alpha]_D^{20}=-93.6$ (c=1, CHCl$_3$).

(R)-(6,6'-Dimethoxybiphenyl-2,2'-diyl)bis[bis(p-methoxyphenyl)phosphine]. M.p. 225°–226°; $[\alpha]_D^{20}=+7.5$ (c=1, CHCl$_3$).

(S)-(6,6'-Dimethoxybiphenyl-2,2'-diyl)bis[bis(p-methoxyphenyl)phosphine]. M.p. 225°–226°; $[\alpha]_D^{20}=-7.3$ (c=1, CHCl$_3$).

(R)-(6,6'-Dimethoxybiphenyl-2,2'-diyl)bis(di-4-biphenylphosphine oxide).

(S)-(6,6'-Dimethoxybiphenyl-2,2'-diyl)bis(di-4-biphenylphosphine oxide).

(R)-(6,6'-Dimethoxybiphenyl-2,2'-diyl)bis(di-4-biphenylphosphine). $[\alpha]_D^{20} = +39$ (c=1, CHCl$_3$).

(S)-(6,6'-Dimethoxybiphenyl-2,2'-diyl)bis(di-4-biphenylphosphine). $[\alpha]_D^{20} = -39.4$ (c=1, CHCl$_3$).

EXAMPLE 8 a) A phenylmagnesium bomide solution prepared from 1.57 g (10.0 mmol) of bromobenzene and 0.243 g (10.0 mmol) of magnesium shavings in 10 ml of tetrahydrofuran was added dropwise at −78° to a solution of 448 mg (1.0 mmol) of (R)-(6,6'-dimethoxybiphenyl-2,2'-diyl)bis(phosphonic acid dichloride) in 100 ml of tetrahydrofuran. After completion of the addition the cooling bath was removed and the reaction mixture was allowed to warm to room temperature. For the working-up, the mixture was treated with sat. NH$_4$Cl solution, the organic phase was separated, washed with sat. NaCl solution, dried over Na$_2$SO$_4$, filtered and evaporated. The residue was taken up in CH$_2$Cl$_2$, the solution was treated with ethyl acetate and the CH$_2$Cl$_2$ was evaporated on a rotary evaporator. Filtration and drying yielded 0.50 g of (R)-(6,6'-dimethoxybiphenyl-2,2'-diyl)bis(diphenylphosphine oxide) as a white powder; $[\alpha]_D^{20} = +127.7$ (c=1, CHCl$_3$).

b) Reduction of this phosphine oxide in an analogous manner to Example 6 gave (R)-(6,6'-dimethoxybiphenyl-2,2'-diyl)bis(diphenylphosphine).

We claim:

1. Racemic and optically active phosphorus compounds of the general formula

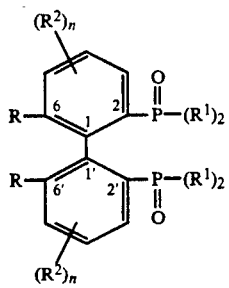

wherein R signifies lower alkyl or protected hydroxy, R$^1$ signifies lower alkoxy, phenoxy, benzyloxy, chlorine or bromine, R$^2$ stands for lower alkyl or lower alkoxy and n represents the number 0, 1 or 2.

2. Racemic and optically active phosphorus compounds in accordance with claim 1, wherein R signifies lower alkyl or protected hydroxy is represented by lower alkoxy.

3. Racemic and optically active phosphorus compounds in accordance with claim 2, wherein n stands for the number 0.

4. Racemic and optically active phosphorus compounds in accordance with claim 3, wherein R$^1$ signifies phenoxy, ethoxy or chlorine and R signifies methoxy or methyl.

5. The phosphorus compound of claim 4 wherein said compound is (RS)-, (R)- or (S)-(6,6'-Dimethoxybiphenyl-2,2'-diyl)bis(phosphonic acid diphenyl ester).

6. The phosphorus compound of claim 4 wherein said compound is (RS)-, (R)- or (S)-(6,6'-Dimethoxybiphenyl-2,2'-diyl)bis(phosphonic acid diethyl ester).

7. The phosphorus compound of claim 4 wherein said compound is (RS)-, (R)- or (S)-(6,6'-Dimethylbiphenyl-2,2'-diyl)bis(phosphonic acid diphenyl ester).

8. The phosphorus compound of claim 4 wherein said compound is (RS)-, (R)- or (S)-(6,6'-Dimethylbiphenyl-2,2'-diyl)bis(phosphonic acid diethyl ester).

9. The phosphorus compound of claim 4 wherein said compound is (RS)-, (R)- or (S)-(6,6'-Dimethoxybiphenyl-2,2'-diyl)bis(phosphonic acid dichloride).

10. The phosphorus compound of claim 1 wherein said phosphorus compound is (RS)-, (R)-, or (S)-[6.6'-bis(methoxymethoxy)biphenyl-2,2'-diyl]bis(phosphonic acid diphenyl ester).

* * * * *